United States Patent
Marziale et al.

(10) Patent No.: US 6,639,967 B2
(45) Date of Patent: Oct. 28, 2003

(54) ELECTRON GUN HEATING CONTROL TO REDUCE THE EFFECT OF BACK HEATING IN MEDICAL LINEAR ACCELERATORS

(75) Inventors: Michael John Marziale, Point Richmond, CA (US); Francisco M. Hernandez-Guerra, Concord, CA (US)

(73) Assignee: Siemens Medical Solutions, USA, Inc., Malvern, PA (US)

( * ) Notice: Subject to any disclaimer, the term of this patent is extended or adjusted under 35 U.S.C. 154(b) by 0 days.

(21) Appl. No.: 09/965,293

(22) Filed: Sep. 27, 2001

(65) Prior Publication Data

US 2003/0058992 A1 Mar. 27, 2003

(51) Int. Cl.[7] .................................................. A61N 5/10
(52) U.S. Cl. ............................ 378/65; 378/97; 378/108
(58) Field of Search .............................. 378/65, 108, 97, 378/4, 64, 117

(56) References Cited

U.S. PATENT DOCUMENTS

| | | | | | |
|---|---|---|---|---|---|
| 5,724,403 A | * | 3/1998 | Siochi et al. | ................ | 378/150 |
| 5,754,622 A | * | 5/1998 | Hughes | ........................ | 378/65 |
| 6,038,284 A | * | 3/2000 | Hernandez-Guerra et al. | ... | 378/65 |
| 6,577,709 B2 | * | 6/2003 | Tarr | ............................ | 378/108 |

* cited by examiner

Primary Examiner—Drew A. Dunn
Assistant Examiner—Irakli Kiknadze

(57) ABSTRACT

A radiation therapy device (2) includes a programmable power source (300) and controller (302) that monitor an injected current level and controls heater voltage in response thereto. The heater voltage is reduced in predetermined increments without affecting the beam profile.

21 Claims, 3 Drawing Sheets

ELECTRON GUN HEATING CONTROL TO REDUCE THE EFFECT OF BACK HEATING IN MEDICAL LINEAR ACCELERATORS

BACKGROUND OF THE INVENTION

The present invention relates to medical linear accelerators and, more particularly, to a system and method for reducing the effects of backheating on the electron gun in a medical linear accelerator.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator including an electron gun and a waveguide is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

An important consideration in delivering radiation treatment is control of the radiation beam. The electron gun is subject to a phenomenon known as "back heating." Backheating causes an increase in the temperature of the electron gun resulting in an increase in the barium evaporation rate (Barium is impregnated into the gun cathode tungsten matrix to enhance electron emission.). This causes a deposition of barium in cavities of the linear accelerator adjacent the electron gun. This, in turn, results in an increase in dark current, which has a deleterious effect on the control of the radiation beam. The net result is that the linear accelerator's useful life is decreased, and therefore must be replaced sooner than would necessarily be desired.

As such, there is a need for controlling the barium evaporation rate in an electron gun. There is a still further need for a medical linear accelerator having a relatively longer useful life.

SUMMARY OF THE INVENTION

These and other problems in the prior art are overcome in large part by a system and method for control of a radiation therapy device according to the present invention.

A radiation therapy device according to an embodiment of the present invention includes a programmable power source and controller that monitor an injected current level and controls heater voltage in response thereto. The heater voltage is reduced in predetermined increments without affecting the beam profile.

A filament voltage controller according to an embodiment of the present invention includes an injector and a remotely programmable electron gun power source. A controller receives an injection trigger signal from the injector, and a measurement of the injection current. The injection current is measured during runup and when RAD ON commences, cuts back the filament voltage a predetermined amount, and measures the current again. So long as the injected current does not fall below the run up level, the heater voltage will be reduced incrementally.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
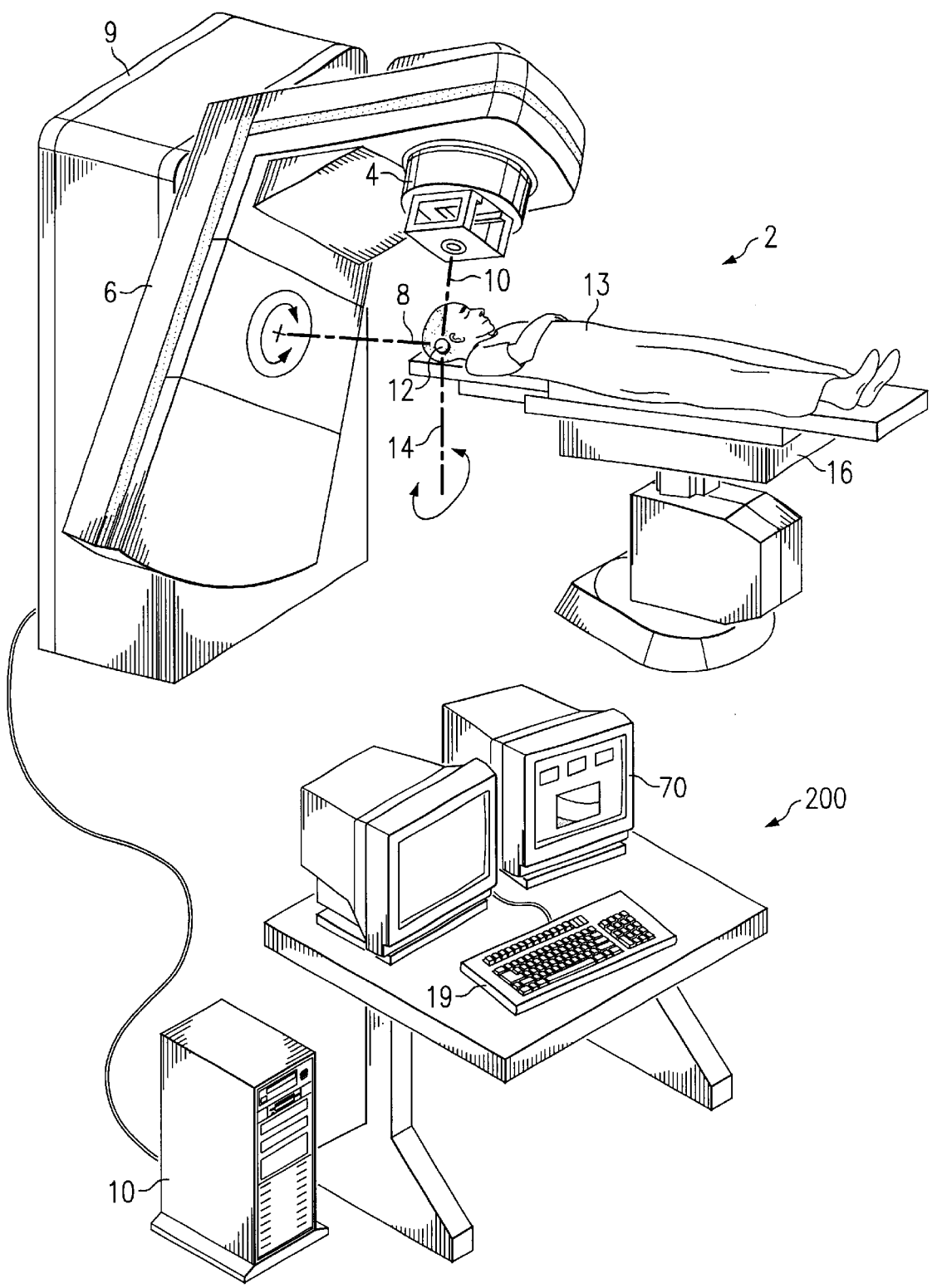
FIG. 1 illustrates an exemplary radiation therapy system according to an implementation of the present invention.

Turning now to the drawings and, with particular attention to FIG. 1, a radiation treatment apparatus embodying the present invention is shown therein and generally identified by reference numeral 2. The radiation therapy apparatus 2 may be a Mevatron or Primus linear accelerator available from Siemens Medical Systems, Inc., Concord, Calif. The radiation treatment apparatus 2 includes a beam shielding device (not shown) within a treatment head 4, a control unit in a housing 9 and a treatment console 200 according to the present invention. The radiation treatment device 2 includes a gantry 6 which can be swiveled around a horizontal axis of rotation 8 in the course of a therapeutic treatment. The treatment head 4 is fastened to a projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment console 200 which is typically located apart from the radiation treatment device 2. The radiation treatment device 2 is normally located in a different room to protect the therapist from radiation. The treatment console 200 includes output devices such as at least one visual display unit or monitor 70 and an input device such as a keyboard 19. Data can be input also through data carriers such as data storage devices or a verification and recording or automatic setup system.

The treatment console 200 is typically operated by the therapist who administers actual delivery of radiation treatment as prescribed by an oncologist by using the keyboard 19 or other input device. The therapist enters into the control unit of the treatment console 200 the data that defines the radiation dose to be delivered to the patient, for example, according to the prescription of the oncologist. The program can also be input via another input device, such a data storage device. Various data can be displayed before and during the treatment on the screen of the monitor 70.

Figure 2:
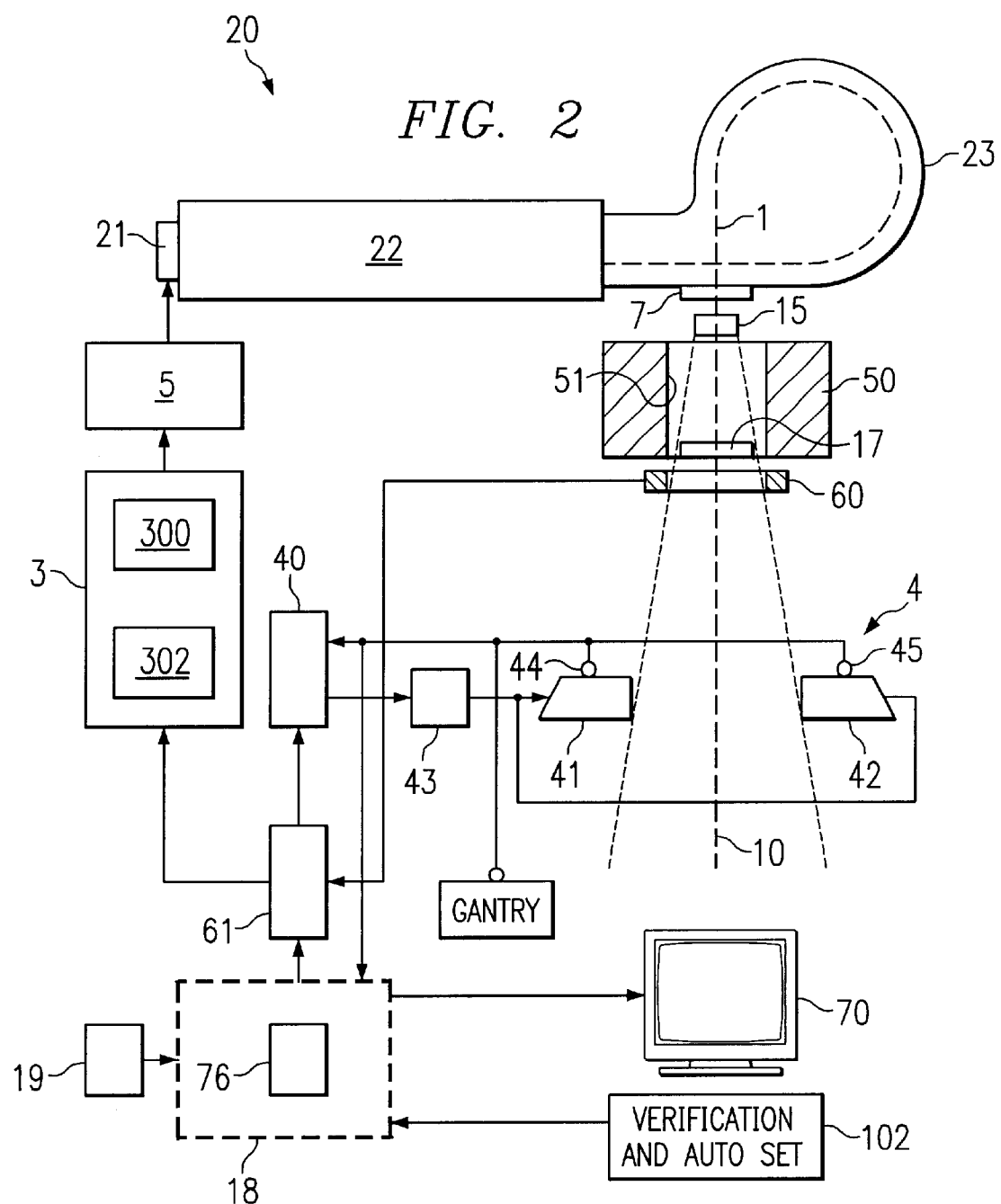
FIG. 2 is a block diagram of a radiation therapy system according to an embodiment of the present invention.

A block diagram of the radiation treatment device 2 and portions of the treatment console 200 are, according to the present invention, illustrated in greater detail in FIG. 2. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source, such as a magnetron or klystron (not shown), is provided, which supplies radio frequency signals for the generation of an electromagnetic field supplied to the waveguide 22. The electrons injected by the injector 5 and emitted by the electron gun 21 are accelerated by this electromagnetic field in the waveguide 22 and exit at the end opposite to electron gun 21 in electron beam 1.

The electron beam 1 enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 may include a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 1 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions.

The plate arrangement 401 may alternatively or additionally include a multi-leaf collimator having many radiation blocking leaves. The leaves of such a multi-leaf collimator include a plurality of opposing leaf or rod pairs, each driven by a motor or drive unit. The drive units move the leaves in and out of the treatment field, thus creating the desired field shape. The rods, or leaves, are relatively narrow, and cast a shadow of about 0.5 to 1. cm at isocenter.

The motor controller 40 is coupled to a dose control unit 61 which includes a dosimetry controller and which is coupled to the processing unit 18 for providing set values for the radiation beam for achieving given isodose curves. The output of the radiation beam is measured by the does measuring chamber 60. In response to deviation between set values and actual values, the dose control unit 61 supplies signals to trigger system 3, which changes in a known manner the pulse repetition frequency.

In addition, as will be explained in greater detail below, the trigger system 3 includes a programmable power source 300 and a signal processing control unit 302 for monitoring and adjusting the injector voltage. The signal processing control unit 302 reads the injected current level and provides a DC representation of the level to the programmable power source 300. The programmable power source 300 then cuts back the heater voltage.

Figure 3:
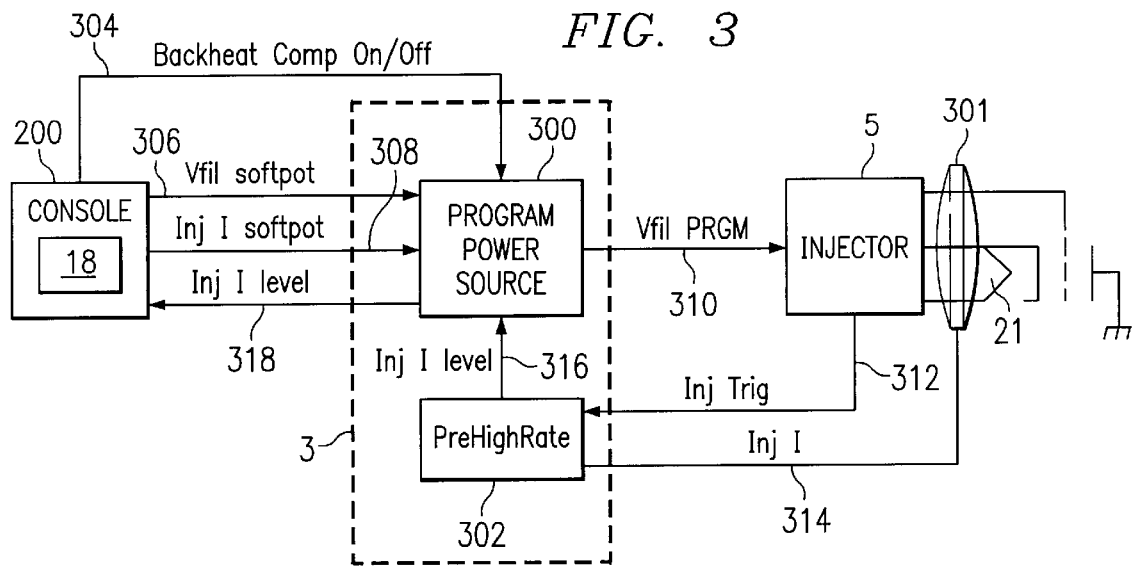
FIG. 3 is a block diagram of an exemplary backheating compensation system for in accordance with an embodiment of the present invention.

More particularly, FIG. 3 is a block diagram showing in greater detail the backheating compensation system of an embodiment of the present invention. The system includes a programmable power source 300 and a signal processing control unit 302 in the trigger system 3, the console treatment console 200, the injector 5, and a current measurement unit 301 at the electron gun 21. The treatment console 200 provides Vfil softpot 306 and Inj I softpot 308 control signals to the programmable power source 300. These may be known control signals used to set the filament voltage and the injector current, respectively. In addition, a backheat comp on/off control signal 304 is used by the treatment console 200 to activate or deactivate the backheating compensation functionality according to embodiments of the present invention. In turn, the programmable power source 300 provides a Vfil prog signal 310 to the injector 5. A current measurement unit 301, which may be implemented as a current transformer, commonly known as a toroid, provides an Inj I signal 314 of the measured injector current to the signal processing unit 302. The signal processing unit 302 may also receive an Inj Trig signal 312 from the injector 5, identifying the triggered pulses. For example, the signal processing unit 302 may include a sample-and-hold circuit which causes a sampling of the Inj I signal 314 each time the Inj Trig signal 312 is received. The signal processing unit 302 provides a DC representation of the injector current to the programmable power source 300. The programmable power source 300 communicates the injector current level to the treatment console 200 as the signal 318.

In operation, the console 200 provides the preprogrammed filament voltage and injector current (FIG. 3) to the programmable power source 300 and turns on the Backheat Comp signal 304 (FIG. 3). The filament voltage is then provided to the injector 5. The current measurement unit 301 provides the measured injector current 314 to the signal processing unit 302. The signal processing unit 302 includes a sample and hold circuit (not shown) to produce a DC representation of the injected current 316 in response to the trigger 312. Measurement of the injector current begins during an initialization phase such as the system RUNUP phase. The programmable power source 300 sends a signal Inj I level 318 to the console 200. When RAD ON commences, the programmable power source 300 cuts back on the filament voltage a preset amount (e.g., 200 mV) and waits a few seconds (e.g., 10) to determine the change in the injected current. As long as the injected current does not fall below a threshold, (as determined, e.g., by the console using the Inj I level signal 318), such as the RUNUP level, the programmable power source 300 will continue to reduce the heater voltage incrementally. A lower threshold may be preprogrammed into the programmable power source 300.

Figure 4:
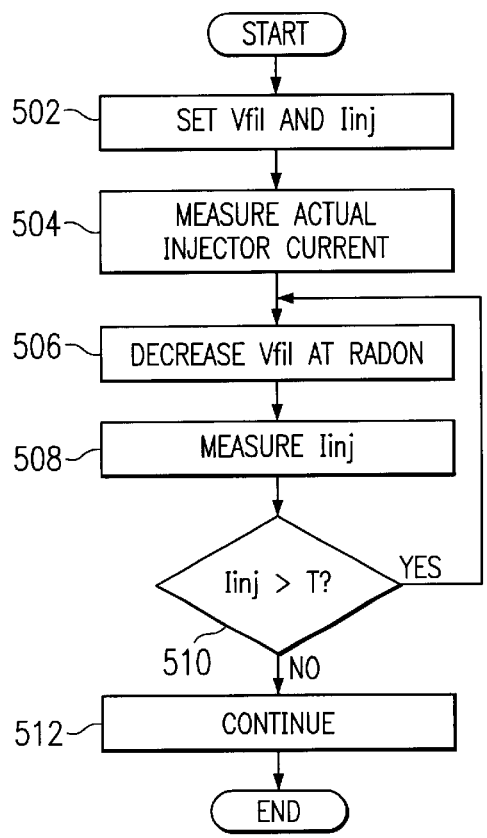
FIG. 4 is a flowchart illustrating operation of an embodiment of the present invention.

FIG. 4 is a flowchart depicting operation of an embodiment of the present invention. In a step 502, the treatment processor 18 of the treatment console 200 sets the filament voltage and the injector current levels. In a step 504, the system measures actual injector current, typically during an initialization or test phase, such as RUNUP. At RAD ON, in step 506, the system decrements the injector voltage by a predetermined amount. At step 508, the system measures the injector current again, typically after a predetermined wait period. In 510, the system then checks to determine if the injector current is greater than a predetermined threshold. For example, the threshold may be the RUNUP current level. If it is, then the system cycles back to decrease the filament voltage in 506. Otherwise, the system will continue treatment using the current injector current level, in step 512.

The invention described in the above detailed description is not intended to be limited to the specific form set forth herein, but is intended to cover such alternatives, modifications and equivalents as can reasonably be included within the spirit and scope of the appended claims.

What is claimed is:

1. A radiation therapy apparatus, comprising:
   an electron gun;

an injector coupled to said electron gun and adapted to provide injector pulses to control said electron gun;

a measurement unit adapted to measure an injector current; and a trigger system adapted to adjust a filament voltage responsive to signals from said measurement unit indicative of said injector current and responsive to activation of a backheating compensation function.

2. A radiation therapy apparatus, comprising:

an electron gun;

an injector coupled to said electron gun and adapted to provide injector pulses to control said electron gun;

a measurement unit adapted to measure an injector current; and a trigger system adapted to adjust a filament voltage responsive to signals from said measurement unit indicative of said injector current, said trigger system including a programmable power source and a signal processing controller for generating a DC signal to said programmable power source responsive to an injector current signal from said current measurement unit and an injection trigger system.

3. A radiation therapy apparatus according to claim 2, said programmable power source adapted to step down s aid filament voltage if said current does not fall below a threshold level.

4. A radiation therapy apparatus in accordance with claim 3, said threshold level being a runup level, sampled before a RAD ON condition.

5. A radiation therapy apparatus according to claim 4, wherein said filament voltage is incrementally stepped down about 200 millivolts.

6. A method for delivering radiation therapy, comprising:

setting a filament voltage and an injector current;

measuring an actual injector current during a run up phase;

incrementally decreasing said filament voltage at RAD ON;

measuring said injector current during a RAD ON phase;

determining if said injector current is greater than a predetermined threshold; and incrementally decreasing said filament voltage if said injector current is above said threshold.

7. A method according to claim 6, wherein said predetermined threshold is an injector current level measured during said run up phase.

8. A method according to claim 6, wherein said incrementally decreasing comprises decreasing said filament voltage by about 200 millivolts.

9. A method according to claim 8, wherein said measuring during said RAD ON phase comprises measuring about 10 seconds after said filament voltage has been decremented.

10. A method, comprising:

providing an electron gun;

providing an injector coupled to said electron gun and adapted to provide injector pulses to control said electron gun;

providing a measurement unit adapted to measure an injector current; and providing a trigger system adapted to adjust a filament voltage responsive to signals from said measurement unit indicative of said injector current and responsive to activation of a backheating compensation function.

11. A method, comprising:

providing an electron gun;

providing an injector coupled to said electron gun and adapted to provide injector pulses to control said electron gun;

providing a measurement unit adapted to measure an injector current; and providing a trigger system adapted to adjust a filament voltage responsive to signals from said measurement unit indicative of said injector current, said trigger system including a programmable power source and a signal processing controller for generating a DC signal to said programmable power source responsive to an injector current signal from said current measurement unit and an injection trigger system.

12. A method according to claim 11, said programmable power source adapted to step down said filament voltage if said current does not fall below a threshold level.

13. A method in accordance with claim 12, said threshold level being a runup level, sampled before a RAD ON condition.

14. A method according to claim 13, wherein said filament voltage is incrementally stepped down about 200 millivolts.

15. A radiation therapy device, comprising:

an electron gun having a filament;

a controller operable to set a filament voltage and an injector current level;

a measuring unit adapted to measure an actual injector current level; and a trigger system adapted to adjust said filament voltage if said actual injector current level is above a predetermined threshold.

16. A device in accordance with claim 15, said trigger system adapted to step down said filament voltage if said current does not fall below a threshold level.

17. A device in accordance with claim 16, said threshold level being a runup level, sampled before a RAD ON condition.

18. A radiation therapy apparatus, comprising:

an electron gun; and a backheating compensation system, comprising:

an injector coupled to said electron gun and adapted to provide injector pulses to control said electron gun;

a measurement unit adapted to measure an injector current; and a trigger system adapted to adjust a filament voltage responsive to signals from said measurement unit indicative of said injector current and responsive to activation of a backheating compensation control signal.

19. A radiation therapy apparatus according to claim 18, said trigger system including a programmable power source and a signal processing controller for generating a control signal to said programmable power source responsive to an injector current signal from said current measurement unit and an injection trigger system.

20. A radiation therapy apparatus according to claim 19, said programmable power source adapted to step down said filament voltage if said current does not fall below a threshold level.

21. A radiation therapy apparatus in accordance with claim 20, said threshold level being a runup level, sampled before a RAD ON condition.

* * * * *